United States Patent
Mehta

(10) Patent No.: US 12,409,065 B2
(45) Date of Patent: Sep. 9, 2025

(54) SYSTEMS AND METHODS FOR IDENTIFYING CASSETTE TYPE IN A SURGICAL SYSTEM

(71) Applicant: Johnson & Johnson Surgical Vision, Inc., Irvine, CA (US)

(72) Inventor: Deep Mehta, Irvine, CA (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 446 days.

(21) Appl. No.: 17/037,342

(22) Filed: Sep. 29, 2020

(65) Prior Publication Data

US 2021/0093482 A1  Apr. 1, 2021

Related U.S. Application Data

(60) Provisional application No. 62/908,548, filed on Sep. 30, 2019.

(51) Int. Cl.
| | | |
|---|---|---|
| *A61F 9/007* | (2006.01) | |
| *A61B 34/00* | (2016.01) | |
| *A61M 1/00* | (2006.01) | |
| *A61M 3/02* | (2006.01) | |

(52) U.S. Cl.
CPC .......... *A61F 9/00745* (2013.01); *A61B 34/25* (2016.02); *A61F 9/00736* (2013.01); *A61M 1/72* (2021.05); *A61M 1/73* (2021.05); *A61M 3/0201* (2021.05); *A61B 2217/007* (2013.01); *A61B 2562/0247* (2013.01); *A61M 1/77* (2021.05)

(58) Field of Classification Search
CPC ...... A61M 1/72; A61M 1/77; A61M 2205/12; A61M 3/0201; A61F 9/007

USPC .......................... 604/35, 30, 31, 32, 33, 34
See application file for complete search history.

(56) References Cited

U.S. PATENT DOCUMENTS

| | | | |
|---|---|---|---|
| 4,758,220 A * | 7/1988 | Sundblom | A61M 1/72 604/35 |
| 4,768,506 A * | 9/1988 | Parker | A61M 1/72 606/174 |
| 4,770,654 A * | 9/1988 | Rogers | A61F 9/00736 604/22 |
| 6,511,454 B1 * | 1/2003 | Nakao | A61M 1/72 604/151 |
| 8,430,841 B2 | 4/2013 | Claus et al. | |
| 9,005,157 B2 | 4/2015 | Gerg et al. | |
| 9,907,901 B2 | 3/2018 | Orczy-Timko et al. | |
| 2004/0074281 A1 * | 4/2004 | Lobdell | G01L 27/007 73/1.57 |

(Continued)

OTHER PUBLICATIONS

International Search Report and Written Opinion for Application No. PCT/IB2020/058526, mailed on Dec. 17, 2020, 6 pages.

*Primary Examiner* — Rebecca E Eisenberg
*Assistant Examiner* — Ted Yang

(57) ABSTRACT

A system for managing phacoemulsification surgery having a cassette with at least one pressure sensor and at least one fluid channel, wherein the at least one pressure sensor is fluidly coupled with the at least one fluid channel. The surgical console also having a controller and a cassette receiving area, for engaging with the cassette, wherein the controller is configured to compare at least one pressure measurement from the at least one pressure sensor to at least one predetermined value indicative of an identifiable cassette type.

11 Claims, 4 Drawing Sheets

(56) References Cited

U.S. PATENT DOCUMENTS

| | | | |
|---|---|---|---|
| 2004/0074282 A1* | 4/2004 | Morgan | A61M 1/74 73/1.71 |
| 2005/0118048 A1* | 6/2005 | Traxinger | A61M 1/72 417/477.2 |
| 2007/0078370 A1* | 4/2007 | Shener | A61M 3/0258 604/8 |
| 2007/0100316 A1 | 5/2007 | Traxinger | |
| 2008/0112828 A1* | 5/2008 | Muri | A61M 1/631 417/477.2 |
| 2008/0114290 A1* | 5/2008 | King | A61M 3/0201 604/30 |
| 2008/0114300 A1* | 5/2008 | Muri | A61M 3/0201 604/118 |
| 2008/0312594 A1* | 12/2008 | Urich | A61M 1/74 604/149 |
| 2009/0158855 A1* | 6/2009 | Holden | A61M 1/73 73/756 |
| 2010/0292631 A1* | 11/2010 | Holden | A61F 9/00745 604/22 |
| 2011/0144567 A1* | 6/2011 | Sorensen | A61F 9/00745 604/22 |
| 2012/0157912 A1* | 6/2012 | Sorensen | A61M 1/77 604/35 |
| 2013/0184638 A1* | 7/2013 | Scarpaci | A61M 1/159 604/28 |
| 2013/0245543 A1* | 9/2013 | Gerg | A61F 9/00736 604/30 |
| 2014/0323953 A1* | 10/2014 | Sorensen | A61F 9/00763 604/35 |
| 2015/0057601 A1* | 2/2015 | Ly | A61M 1/288 73/198 |
| 2016/0022545 A1 | 1/2016 | Boulanger et al. | |
| 2016/0367735 A1* | 12/2016 | Eddo | A61M 39/22 |
| 2017/0189231 A1* | 7/2017 | Baxter | A61M 1/77 |
| 2018/0092774 A1* | 4/2018 | Mehta | A61B 3/16 |
| 2019/0099526 A1* | 4/2019 | Hajishah | A61M 3/0201 |
| 2019/0099529 A1* | 4/2019 | Mehta | A61M 1/74 |
| 2019/0099546 A1* | 4/2019 | Keh | A61M 1/743 |
| 2019/0099547 A1* | 4/2019 | Mehta | A61F 9/00745 |
| 2019/0099548 A1* | 4/2019 | Mehta | A61M 3/0202 |

* cited by examiner

SYSTEMS AND METHODS FOR IDENTIFYING CASSETTE TYPE IN A SURGICAL SYSTEM

CROSS-REFERENCE TO RELATED APPLICATIONS

This application claims priority to U.S. Provisional Patent Application No. 62/908548, filed on Sep. 30, 2019, the entire contents of which are hereby incorporated by reference.

BACKGROUND OF THE INVENTION

Field of Technology

The present invention relates generally to the use of a cassette in a surgical console and, more specifically, to the systems and methods for identifying a cassette for use in a surgical console.

Description of the Background

The optical elements of the eye include both a cornea (at the front of the eye) and a lens within the eye. The lens and cornea work together to focus light onto the retina at the back of the eye. The lens also changes in shape, adjusting the focus of the eye to vary between viewing near objects and far objects. The lens is found just behind the pupil and within a capsular bag, the capsular bag being a thin, relatively delicate structure which separates the eye into anterior and posterior chambers.

With age, clouding of the lens or cataracts is fairly common. Cataracts may form in the hard central nucleus of the lens, in the softer peripheral cortical portion of the lens, or at the back of the lens near the capsular bag. Cataracts can be treated by the replacement of the cloudy lens with an artificial lens. Phacoemulsification systems often use ultrasound energy to fragment the lens and aspirate the lens material from within the capsular bag. This may allow the capsular bag to be used for positioning of the artificial lens and maintains the separation between the anterior portion of the eye and the vitreous humor in the posterior chamber of the eye.

During cataract surgery and other therapies of the eye, accurate control over the volume of fluid within the eye is highly beneficial. For example, while ultrasound energy breaks up the lens and allows it to be drawn into a treatment probe with an aspiration flow, a corresponding irrigation flow may be introduced into the eye so that the total volume of fluid in the eye does not change excessively. If the total volume of fluid in the eye is allowed to get too low at any time during the procedure, the eye may collapse and cause significant tissue damage. Similarly, excessive pressure within the eye may strain and injure tissues of the eye.

While a variety of specific fluid transport mechanisms may be used in phacoemulsification and other treatment systems for the eyes, aspiration flow systems can generally be classified in two categories: 1) volumetric-based aspiration flow systems using positive displacement pumps (e.g. peristaltic); and 2) vacuum-based aspiration systems using a vacuum source, typically applied to the aspiration flow through an air-liquid interface within a reservoir (e.g. Venturi). Both systems may be incorporated into one treatment system and/or cassette. Cassette ("pack") systems can be used to couple peristaltic pump drive rotors and/or vacuum systems of the surgical consoles to an eye treatment handpiece, with the flow network conduit of the cassette being disposable to avoid cross-contamination between different patients.

In traditional ophthalmic surgery, fluid from the fluid source is also used to irrigate the eye during a procedure. As mentioned above, the irrigation fluid serves to maintain proper intraocular pressure and to replace fluid during aspiration of emulsified lens fragments. The irrigation source is may be a 500 ml bottle or drip bag of saline solution or a pressurized infusion source. One issue is that, during ophthalmic surgery, the potential exists for the saline solution to be depleted, turning the irrigation dry. Though an unlikely scenario, the potential consequences are substantial—severe cornmeal burns, capsular tear requiring vitrectomy or additional vitro-retinal surgery, damage to the structure of the eye, and/or loss of vision.

To mitigate such occurrences, staff operating a system typically begins each procedure with a fresh irrigation source prior to each case and monitor the fluid visually throughout surgery. In some instances, flow sensors are used to measure flow out of the irrigation source. However, conventional configurations do not efficiently provide relative irrigation source volumes and only provide warnings when a detected flow indicates a very low irrigation source volume. As such, improvements are needed in the art to address these issues.

SUMMARY

A system for managing phacoemulsification surgery, the system comprising a cassette comprising at least one pressure sensor and at least one fluid channel, wherein the at least one pressure sensor is fluidly coupled with the at least one fluid channel; a surgical console comprising a controller and a cassette receiving area, for engaging with the cassette; wherein the controller is configured to compare at least one pressure measurement from the at least one pressure sensor to at least one predetermined value indicative of an identifiable cassette type.

Under another exemplary embodiment, a system for identifying a surgical cassette in a phacoemulsification surgery, the system comprising a cassette having one or more fluid channels, at least one pressure sensor, and aspiration tubing; wherein the at least one pressure sensor is in fluid communication with the one or more fluid channels and the aspiration tubing; and a surgical console comprising a controller and a cassette receiving area for engaging the cassette; wherein the controller is configured to record a plurality of pressure measurements from the at least one pressure sensor during an unoccluded vacuum applied to the cassette and compare the plurality of pressure measurements to a predetermined value indicative of an identifiable cassette type; and wherein the predetermined value is a function of flow rate and restriction to flow caused by an inner diameter of the aspiration tubing, the one or more fluid channels, or both.

DESCRIPTION OF THE DRAWINGS

The accompanying drawings are included to provide a further understanding of the invention and are incorporated in and constitute a part of this specification. The drawings illustrate disclosed embodiments and/or aspects and, together with the description, serve to explain the principles of the invention, the scope of which is determined by the claims.

DETAILED DESCRIPTION OF THE INVENTION

Figure 1A:
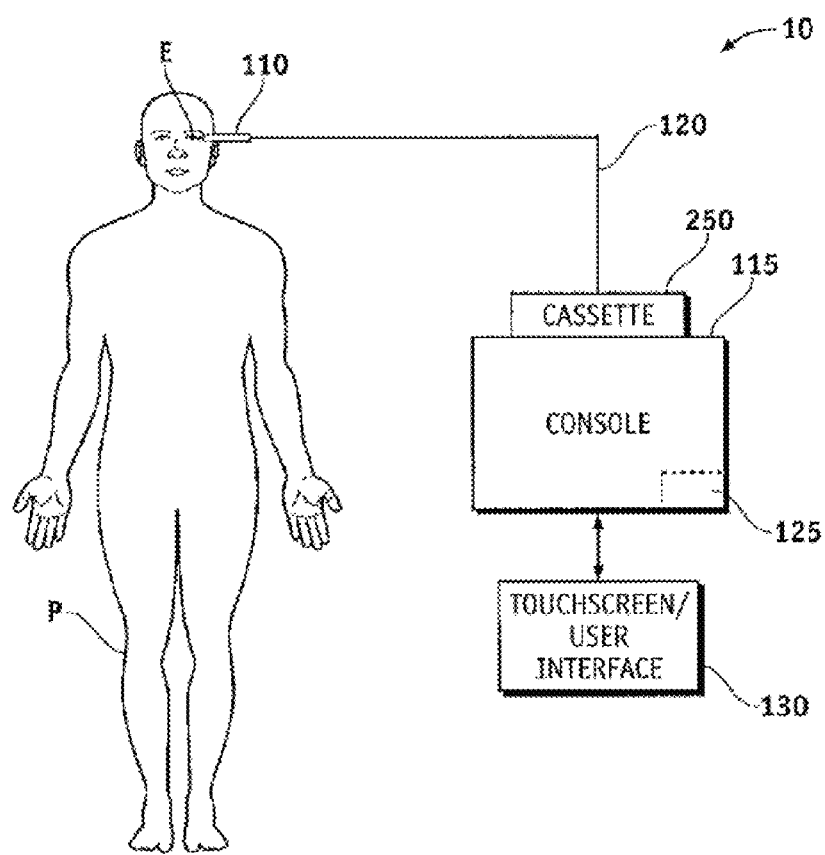
FIG. 1A is a schematic illustrating an eye treatment system in which a cassette is coupled to an eye treatment probe with an eye treatment console under one embodiment.

It is to be understood that the figures and descriptions of the present invention have been simplified to illustrate elements that are relevant for a clear understanding of the present invention, while eliminating, for the purpose of clarity, many other elements found in typical surgical, and particularly optical surgical, apparatuses, systems, and methods. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to the disclosed elements and methods known to those skilled in the art.

The figures and descriptions provided herein may have been simplified to illustrate aspects that are relevant for a clear understanding of the herein described apparatuses, systems, and methods, while eliminating, for the purpose of clarity, other aspects that may be found in typical similar devices, systems, and methods. Those of ordinary skill may thus recognize that other elements and/or operations may be desirable and/or necessary to implement the devices, systems, and methods described herein. But because such elements and operations are known in the art, and because they do not facilitate a better understanding of the present disclosure, for the sake of brevity a discussion of such elements and operations may not be provided herein. However, the present disclosure is deemed to nevertheless include all such elements, variations, and modifications to the described aspects that would be known to those of ordinary skill in the art.

Embodiments are provided throughout so that this disclosure is sufficiently thorough and fully conveys the scope of the disclosed embodiments to those who are skilled in the art. Numerous specific details are set forth, such as examples of specific components, devices, and methods, to provide a thorough understanding of embodiments of the present disclosure. Nevertheless, it will be apparent to those skilled in the art that certain specific disclosed details need not be employed, and that exemplary embodiments may be embodied in different forms. As such, the exemplary embodiments should not be construed to limit the scope of the disclosure. As referenced above, in some exemplary embodiments, well-known processes, well-known device structures, and well-known technologies may not be described in detail.

A surgical cassette, also referred to as a medical pack, a fluidic cassette, or simply, a cassette or pack, is used to facilitate irrigation and aspiration during surgical procedures, such as phacoemulsification surgery. The surgical cassette may be inserted and mounted to a surgical console and become part of an overall phacoemulsification surgery system. The surgical cassette may perform a myriad of functions, such as effluent material collection, fluid channel pressure sensing, and control the flow of fluid through tubing encased within the cassette and between a surgical handpiece and a surgical console.

A surgical cassette typically comprises a front plate, a back plate, and a gasket between, at least partially, the back plate and the front plate. Molded within either/or the front plate and the back plate may be fluid channels/pathways, e.g. creating desired pathways between one of the front plate or the back plate and the gasket. The gasket may comprise one or more valves and one or more sensors to promote fluid flow through the tubing along the desired pathways. In another embodiment, at least a portion of the fluid channels/pathways in the surgical cassette may be tubing. In another embodiment, the fluid channels/pathways may be created by mating the front plate with the back plate without a gasket and sealing the front plate and back plate together. In addition, the surgical cassette may be coupled to irrigation tubing and aspiration tubing that fluidly connects the cassette with other features of a surgical system, such as an irrigation fluid source, a surgical handpiece, and one or more pumps.

Surgical cassettes may utilize different types of sensors to monitor pressure of certain fluid lines during the surgical process. Other single use cassettes may use a low cost pressure diaphragm on the cassette with a console mounted Linear Variable Differential Transformer (LVDT) to measure the deflection of the pressure diaphragm with either a low rate spring pushing the LVDT against the surface of the pressure diaphragm or a magnet coupling the LVDT to the surface of the diaphragm, or a combination of both a spring and magnet. The spring force and/or friction force associated with movement of the LVDT sensing element reduces the accuracy and repeatability of this type system. Other systems may use laser triangulation displacement sensors to measure the deflection of a pressure diaphragm.

Referring now to FIG. 1A, a system 10 for treating an eye E of a patient P generally includes an eye treatment probe handpiece 110 coupled with a console 115 by a cassette 250. Handpiece 110 generally includes a handle for manually manipulating and supporting an insertable probe tip. The probe tip has a distal end which is insertable into the eye, with one or more lumens in the probe tip allowing irrigation fluid to flow from console 115 and/or cassette 250 into the eye. Aspiration fluid may also be withdrawn through a lumen of the probe tip, with console 115 and cassette 250 generally including a vacuum aspiration source, a positive displacement aspiration pump, or both to help withdraw and control a flow of surgical fluids into and out of eye E. As the surgical fluids may include biological materials that should not be transferred between patients, cassette 250 will often comprise a sterilizable (or alternatively, disposable) structure, with the surgical fluids being transmitted through flexible conduits 120 of cassette 250 that avoid direct contact in between those fluids and the components of console 115.

When a distal end of the probe tip of handpiece 110 is inserted into an eye E, for example, for removal of a lens of a patient P with cataracts, an electrical conductor and/or pneumatic line (not shown) may supply energy from console 115 to an ultrasound transmitter of handpiece 110, a cutter mechanism, or the like. Alternatively, handpiece 110 may be configured as an irrigation/aspiration (I/A) and/or vitrectomy handpiece. Also, the ultrasonic transmitter may be replaced by other means for emulsifying a lens, such as a high energy laser beam. The ultrasound energy from handpiece 110 helps to fragment the tissue of the lens, which can then be drawn into a port of the tip by aspiration flow. So as to balance the volume of material removed by the aspiration flow, an irrigation flow through handpiece 110 (or a separate probe structure) may also be provided, with both the aspiration and irrigation flows being controlled by console 115.

To avoid cross-contamination between patients without incurring excessive expenditures for each procedure, cassette 250 and its flexible conduits 120 may be disposable. However, the flexible conduit or tubing may be disposable, with the cassette body and/or other structures of the cassette being sterilizable. Cassette 250 may be configured to interface with reusable components of console 115, including, but not limited to, peristaltic pump rollers, a Venturi or other vacuum source, a controller 125, and/or the like.

Console 115 may include controller 125, which may include an embedded microcontroller and/or many of the components common to a personal computer, such as a processor, data bus, a memory, input and/or output devices (including a user interface 130 (e.g. touch screen, graphical user interface (GUI), etc.), and the like. Controller 125 will often include both hardware and software, with the software typically comprising machine readable code or programming instructions for implementing one, some, or all of the methods described herein. The code may be embodied by a tangible media such as a memory, a magnetic recording media, an optical recording media, or the like. Controller 125 may have (or be coupled with) a recording media reader, or the code may be transmitted to controller 125 by a network connection such as an internet, an intranet, an ethernet, a wireless network, or the like. Along with programming code, controller 125 may include stored data for implementing the methods described herein and may generate and/or store data that records parameters corresponding to the treatment of one or more patients.

Figure 1B:
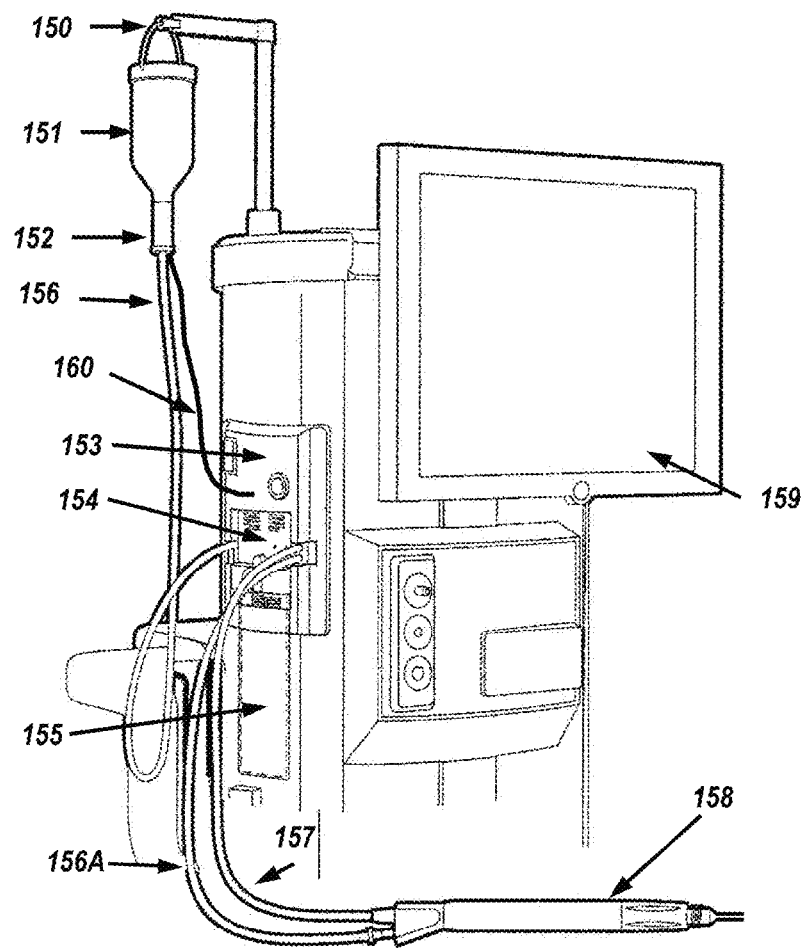
FIG. 1B is a schematic illustrating a surgical eye treatment console under another exemplary embodiment.

Referring now to FIG. 1B, a simplified surgical console is illustrated, where a fluid path may be demonstrated under an exemplary embodiment. In this example, an irrigation source 151 may be configured as a bottle or bag hanging from an IV pole hanger 150. It is understood by those skilled in the art that, while an integrated IV pole is illustrated, other configurations, utilizing standalone/static IV poles, or other suitable configurations, e.g. a pressurized infusion source, are contemplated by the present disclosure.

An exemplary irrigation path for fluid may be realized via surgical cassette 154 having cassette interface 153, which receives fluid from irrigation source 151 via drip chamber 152. Irrigation line 156A and aspiration line 157 are coupled to handpiece 158. Irrigation fluid may flow from drip chamber 152 through the irrigation tubing into surgical cassette 154. Irrigation fluid may then flow from the surgical cassette through handpiece irrigation line 156A which may be coupled to an irrigation port on handpiece 158. Aspirated fluid may flow from handpiece aspiration line 157 back to surgical cassette 154 and into a waste collection bag 155. A touch screen display 159 may be provided to display system operation conditions and parameters, and may include a user interface (e.g., touch screen, keyboard, track ball, mouse, etc.—see controller 125 of FIG. 1A) for entering data and/or instructions to the system of FIG. 1B.

Figure 2:
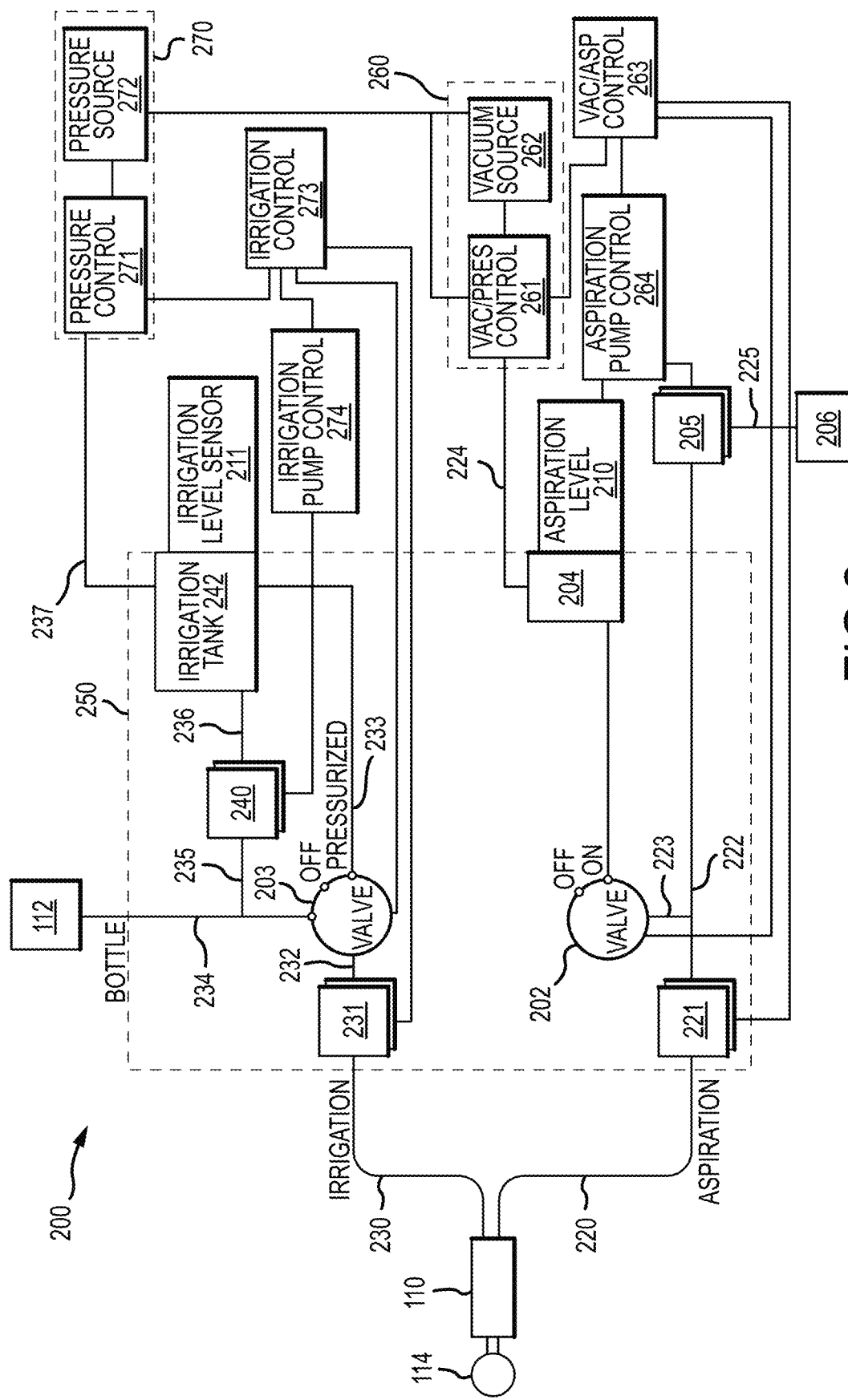
FIG. 2 is a functional block diagram of an exemplary cassette system for an eye treatment system under one embodiment.

Referring to FIG. 2, an exemplary cassette system showing some of the components and interfaces that may be employed in a phaco system, such as ones illustrated in FIGS. 1A-B. Handpiece 110 may be connected to (or coupled with) the input side of vacuum pressure sensor 221, typically by fluid pathways such as fluid pathway 220. The output side of vacuum pressure sensor 221 is connected to valve 202 within cassette 250 via fluid pathway 222. The exemplary embodiment may configure valve 202 to interface between handpiece 110, vacuum tank 204, pump 205, which may be a peristaltic pump but may be another type of pump, and collection 206. In this configuration, the system may operate valve 202 (which may be for example, a flow selector valve) to connect handpiece 110 with vacuum tank 204 and/or with pump 205 based on signals received from console 115 resulting from the surgeon's input, e.g. via user interface 130 or a foot pedal (not shown). As discussed herein in greater detail, an aspiration level sensor 210 may be communicatively coupled to vacuum tank 204.

The valve 202 illustrated in FIG. 2 may provide a connection between vacuum tank 204 and fluid pathway 222. The exemplary embodiment is not limited to one valve and may be realized using two valves each having at least two output ports, possibly connected together to provide the functionality described herein. For example, a pair of two valves may be configured in a daisy chain arrangement, where the output port of a first valve is directly connected to the input port of a second valve. Console 115 may operate both valves together to provide three different flow configurations. For example, using two valves, valve one and valve two, valve one may use output port one, which is the supply for valve two. Valve two may connect to one of two ports providing two separate paths. When valve one connects its input port to its second output port rather than the output port that directs flow to the second valve, a third path is provided. It is also envisioned that valve 202 may be or comprise one or more pinch valves. The one or more pinch valves may be located along fluid pathway 220, 222 and/or 223, or any other fluid pathway as discussed herein. In an embodiment, the one or more valves may be a rotary valve or any other valve known in the art.

Console 115 may also comprise vacuum pressure center 260 which may provide a vacuum through fluid pathway 224 to vacuum tank 204. The vacuum provided through fluid pathway 224 may be regulated by control module 261 based on signals received from aspiration control module 263 which may result from the surgeon's input to user interface 130 (or any other input means, e.g. a foot pedal) and/or based on other signals received from vacuum pressure sensor 221. Aspiration control module 263 may also control pump control 264 and allow for operation of pump 205 for the movement of fluid from both the handpiece 110 and the vacuum tank 204 to collector 206 via pathway 225.

In the configuration shown, vacuum pressure center 260 includes a vacuum source 262, such as a venturi pump and an optional control module 261 (and valve (not shown)), but other configurations are possible. In this arrangement, vacuum pressure center 260 may operate to remove air from the top of vacuum tank 204 and deliver the air to atmosphere (not shown). Removal of air from vacuum tank 204 in this manner may reduce the pressure within the tank, which may reduce the pressure in the attached fluid pathway 220, to a level less than the pressure within eye 114. A lower reservoir pressure connected through valve 202 may cause fluid to move from the eye, thereby providing aspiration.

Thus, while a single valve 202 is illustrated in FIG. 2 associated with aspiration, it is to be understood that this illustration represents a valve arrangement, including one or more valves (such as a flow selector valve) performing the functionality described herein, and is not limited to a single device or a single valve. In the exemplary vacuum pressure sensor 221, a strain gauge or other suitable component may communicate or signal information to console 115 to provide an amount of vacuum sensed in the handpiece fluid pathway 220. Console 115 may determine the actual amount of vacuum present based on the communicated information.

Vacuum pressure sensor 221 monitors flow into and out of the line, and can be used to determine when flow should be reversed, such as encountering a certain pressure level (e.g. in the presence of an occlusion), and based on values obtained from the vacuum pressure sensor 221, the system may control valve 202 and the pumps illustrated. It is to be understood that while components presented in FIG. 2 and other drawings of the present application are not shown connected to other system components, such as console 115, they are in fact connected for the purpose of monitoring and control of the components illustrated.

With respect to vacuum pressure sensor 221, emergency conditions such as a dramatic drop or rise in pressure may result in a type of fail-safe operation. The exemplary embodiment employs vacuum pressure sensor 221 to monitor the flow conditions and provide signals representing flow conditions to the system such as via console 115 for the purpose of controlling components shown including but not limited to valve 202 and the pumps shown. The fluid channels/pathways or flow segments of surgical cassette system 200 may include the fluid connections, for example molded fluid channels and/or flexible tubing, between each component represented with solid lines in FIG. 2.

Handpiece 110 may be connected to (or coupled with) the output side of irrigation pressure sensor 231, typically by fluid pathways such as fluid pathway 230. The input side of irrigation pressure sensor 231 is connected to valve 203 (such as for example, a flow selector valve) within cassette 250 via fluid pathway 232. The exemplary embodiment may configure valve 203 to interface between handpiece 110, irrigation tank 242, pump 240, which may be a peristaltic pump but may be another type of pump, and irrigation fluid source 112. In this configuration, the system may operate valve 203 to connect handpiece 110 with gravity feed or pressurized irrigation based on signals received from console 115 resulting from the surgeon's input to user interface 130.

The valve 203 illustrated in FIG. 2 may provide a connection between irrigation tank 242, irrigation fluid source 112, and fluid pathway 232. The exemplary embodiment is not limited to one valve and may be realized using two valves each having at least two output ports, possibly connected together to provide the functionality described herein. For example, a pair of two valves may be configured in a daisy chain arrangement, where the output port of a first valve is directly connected to the input port of a second valve. Console 115 may operate both valves together to provide three different flow configurations. For example, using two valves, valve one and valve two, valve one may use output port one, which is the supply for valve two. Valve two may connect to one of two ports providing two separate paths. When valve one connects its input port to its second output port rather than the output port that directs flow to the second valve, a third path is provided. It is also envisioned that valve 203 may be or comprise one or more pinch valves. The one or more pinch valves may be located along fluid pathway 230, 232, 233, 234 and/or 235, or any other fluid pathway as discussed herein. In an embodiment, one or more of the valves may be a rotary valve or any other valve known in the art.

Console 115 may also comprise irrigation pressure center 270 which may provide a positive pressure through fluid pathway 237 to irrigation tank 242 using an applied pressure from pressure source 272. The pressure provided through fluid pathway 237 may be regulated by control module 271 based on signals received from irrigation control module 273 which may result from the surgeon's input to user interface 130 and/or based on other signals received from vacuum pressure sensor 231. Irrigation control module 273 may also control pump control 274 and allow for operation of pump 240 for the movement of fluid from irrigation fluid source 112 to collector irrigation tank 242 via pathway 236. As discussed herein in greater detail, an irrigation level sensor 211 may be communicatively coupled to irrigation tank 242.

While a single valve 203 is illustrated in FIG. 2 associated with irrigation, it is to be understood that this illustration represents a valve arrangement, including one or more valves performing the functionality described herein, and is not limited to a single device or a single valve. In the exemplary irrigation pressure sensor 231, a strain gauge or other suitable component may communicate or signal information to console 115 to provide an amount of vacuum sensed in the handpiece fluid pathway 230. Console 115 may determine the actual amount of vacuum present based on the communicated information.

Console 115, for example, may support two different cassette types. One cassette type may provide flow-based aspiration (e.g. peristaltic), another cassette type may provide vacuum-based aspiration (e.g. Venturi), and another type may provide both flow-based and vacuum-based aspiration. Cassettes within each of these groups may also vary in other ways, including, for example, the size and shape of the fluid channels/pathways that is used within each cassette body and the tubing (e.g. irrigation tubing and aspiration tubing) associated with the cassette. Traditionally, a mechanical switch operated by a user of the surgical console is used to identify between cassette types. For example, when a flow-based only cassette is inserted and a mechanical switch is operated to identify the cassette as a flow-based only cassette, the system may disable all vacuum-based mode settings and operation. Similarly, when a dual mode cassette is inserted and a mechanical switch is operated to identify the cassette as a dual mode cassette, the system may provide both flow-based and vacuum-based aspiration.

By using techniques other than a mechanical switch associated with console, the present invention may allow a console to perform any number of actions once the inserted cassette type is known, including, but not limited to, disabling usage of certain type of cassettes, setting certain flow rate and vacuum parameters, enabling certain features such as dual mode aspiration or irrigation, and enabling collection of certain parameters based on the type of cassette detected, for example. As described above and more fully below, the present invention may allow for system parameters and surgeon programs associated with the surgical console to be optimized based on type of cassette is inserted.

The present invention may induce a surgical system to conduct a series of running aspiration vacuum measurements during a cassette prime sequence to identify the type of cassette. More specifically, when a cassette is captured in the surgical console, the system may begin the cassette prime sequence by commanding a series of aspiration flow rates for certain periods and recording measurements on the resulting running vacuum. The unoccluded running aspiration vacuum may be a function of flow rate and restriction to flow caused by the inner diameter (I.D.) of the fluid channels/tubing associated with the captured cassette. Typically, the running vacuum increases for given fluid flow rate as the inner diameter of the fluid channels/tubing decreases. The system will be able to identify the type of cassette based on at least one of the recorded measurements taken during a prime sequence and comparing at least one of the measurements to a list of known or predetermined values associated with the priming of cassettes having fluid channels/tubing of known diameter, for example. In general, measurements of various cassettes are influenced by the inner diameter of the aspiration tubing and/or fluid channels associated with the particular cassette and are statistically distinct given that the inner diameter of fluid channels/tubing used in various cassettes is significantly different between the cassettes.

The present invention employs various known fluidics principles which may help to identify cassette types without requiring any changes to the cassette manifold, fluidics interface panel or mechanical assembly. Simply put, the present invention may be used with any existing surgical console where a removable cassette having operable fluid channels and/or tubing is used. In an embodiment of the present invention, the aspiration tubing and/or fluid channels of a cassette may have an inside diameter that is statistically different as between identifiable cassette types such that the present invention may detect differences between running vacuums for a given flow rate as between cassettes of different types.

Figure 3:
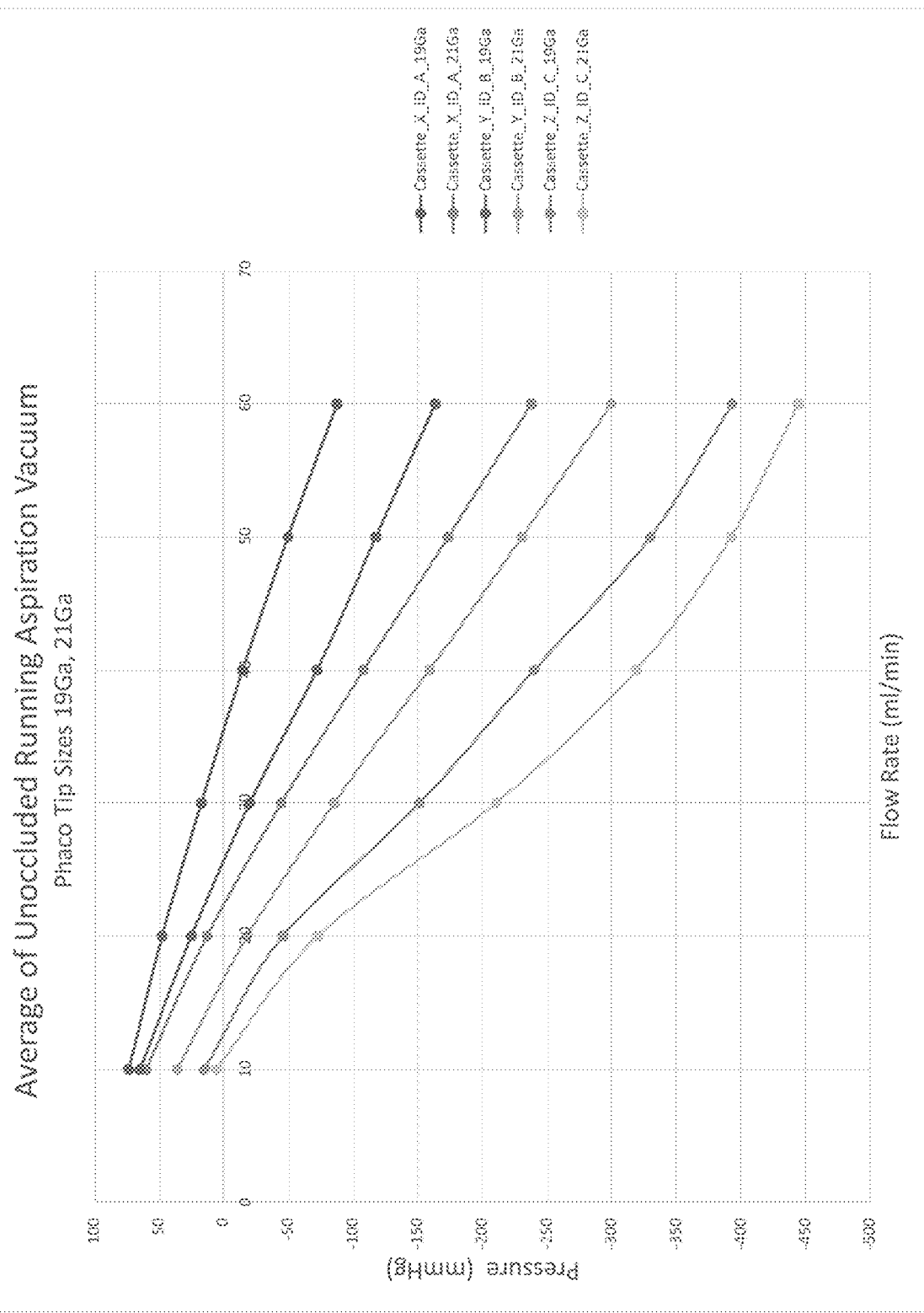
FIG. 3 is a schematic illustrating cassette measurements under another exemplary embodiment.

As illustrated in FIG. 3, the running aspiration vacuum may be different for given flow rate within a given cassette having aspiration tubing and/or fluid channels of certain inner diameters and various phaco tips. The present invention may perform a series of running aspiration vacuum measurement as part of cassette prime sequence starting at an aspiration flow rate of about 10 ml/min and ending at about 80 ml/min at about 10 ml/min intervals. These running vacuum measurements may be compared against expected ranges for each flow rate for given cassette with specified aspiration inner diameter. For each flow rate, an average of running vacuum measurements may differ based on the inner diameter of the aspiration tubing and/or fluid channels. The system may use this information to identify type of cassette inserted into the surgical console.

The present invention may take any number of actions once the type of cassette is identified including, but not limited to, disabling usage of certain type of cassettes, setting certain flow rate and vacuum parameters, enabling certain feature such as dual mode aspiration or irrigation, and/or enabling collection of certain parameters based on type of cassette. System parameters and surgeon programs may be optimized based on type of cassette is inserted. In an embodiment, a surgical system with two pressure transducers for both irrigation pressure and aspiration pressure/vacuum may perform additional measurements on irrigation and aspiration tubing and/or fluid channels associated with a cassette to optimize certain surgeon program settings.

Those of skill in the art will appreciate that the herein described apparatuses, engines, devices, systems and methods are susceptible to various modifications and alternative constructions. There is no intention to limit the scope of the invention to the specific constructions described herein. Rather, the herein described systems and methods are intended to cover all modifications, alternative constructions, and equivalents falling within the scope and spirit of the disclosure, any appended claims and any equivalents thereto.

In the foregoing detailed description, it may be that various features are grouped together in individual embodiments for the purpose of brevity in the disclosure. This method of disclosure is not to be interpreted as reflecting an intention that any subsequently claimed embodiments require more features than are expressly recited.

Further, the descriptions of the disclosure are provided to enable any person skilled in the art to make or use the disclosed embodiments. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein, but rather is to be accorded the widest scope consistent with the principles and novel features disclosed herein.

What is claimed is:

1. A system for managing phacoemulsification surgery, the system comprising:
   a cassette comprising at least one pressure sensor and at least one fluid channel, wherein the at least one pressure sensor is fluidly coupled with the at least one fluid channel;
   a surgical console comprising a controller and a cassette receiving area, for engaging with the cassette;
   wherein the controller is configured to:
      identify a cassette type from among a first identifiable cassette type, a second identifiable cassette type, or a third identifiable cassette type by performing a series of running aspiration vacuum measurements during a cassette prime sequence and comparing at least one pressure measurement from the at least one pressure sensor to at least one predetermined value indicative of one of the first identifiable cassette type, the second identifiable cassette type, or the third identifiable cassette type, and
      control a positive displacement pump and a vacuum source based on the cassette type identified;
   wherein the first identifiable cassette type is configured to provide flow-based aspiration in the at least one fluid channel,
   wherein, the second identifiable cassette type is configured to provide vacuum-based aspiration in the at least one fluid channel, and
   wherein the third identifiable cassette type is configured to provide both the flow-based aspiration and the vacuum-based aspiration in the at least one fluid channel.

2. The system of claim 1, wherein the predetermined value is derived from at least one flow rate associated with the first identifiable cassette type or the second identifiable cassette type.

3. The system of claim 1, wherein the at least one pressure measurement occurs when a measurable flow rate is greater than 10 mil/min.

4. The system of claim 1, wherein the at least one pressure measurement occurs when a measurable flow rate is less than 80 mil/min.

5. The system of claim 1, wherein an inner diameter of the at least one fluid channel is less than 0.10 inch.

6. The system of claim 1, wherein an inner diameter of the at least one fluid channel is greater than 0.10 inch.

7. The system of claim 1, wherein an outer diameter of the at least one fluid channel is less than 0.20 inch.

8. The system of claim 1, wherein the fluid channel is aspiration tubing.

9. The system of claim 8, wherein an unoccluded vacuum is between about −80 mmHg and −440 mmHg.

10. The system of claim 8, wherein an inner diameter of the aspiration tubing is less than 0.10 inch.

11. The system of claim 1, wherein the at least one pressure measurement is an aspiration vacuum measurement.

\* \* \* \* \*